US012122747B2

(12) United States Patent
Jeong et al.

(10) Patent No.: US 12,122,747 B2
(45) Date of Patent: Oct. 22, 2024

(54) DIESTER-BASED MATERIAL PRODUCTION UNIT AND DIESTER-BASED MATERIAL PRODUCTION SYSTEM INCLUDING THE SAME

(71) Applicant: LG CHEM, LTD., Seoul (KR)

(72) Inventors: Jae Hun Jeong, Daejeon (KR); Sung Kyu Lee, Daejeon (KR); Yeon Uk Choo, Daejeon (KR); Seok Goo Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 586 days.

(21) Appl. No.: 17/603,549

(22) PCT Filed: Jul. 2, 2020

(86) PCT No.: PCT/KR2020/008674
§ 371 (c)(1),
(2) Date: Oct. 13, 2021

(87) PCT Pub. No.: WO2021/002705
PCT Pub. Date: Jan. 7, 2021

(65) Prior Publication Data
US 2022/0213019 A1    Jul. 7, 2022

(30) Foreign Application Priority Data

Jul. 4, 2019   (KR) .................. 10-2019-0080462

(51) Int. Cl.
*C07C 67/08*   (2006.01)
*B01D 17/02*   (2006.01)
(Continued)

(52) U.S. Cl.
CPC .......... *C07C 67/08* (2013.01); *B01D 17/0214* (2013.01); *B01D 19/0036* (2013.01);
(Continued)

(58) Field of Classification Search
CPC ......... C07C 67/02; C07C 67/08; C07C 69/80; C07C 69/82; C07C 69/34; B01J 19/0013;
(Continued)

(56) References Cited

U.S. PATENT DOCUMENTS 3,476,796 A  * 11/1969 Adachi ................... C07C 67/08
                                                                560/99
5,786,443 A      7/1998 Lowe
(Continued)

FOREIGN PATENT DOCUMENTS

JP       09-295958 A      11/1997
JP       2002-88020 A      3/2002
(Continued)

*Primary Examiner* — Yate' K Cutliff
(74) *Attorney, Agent, or Firm* — Bryan Cave Leighton Paisner LLP

(57) ABSTRACT

The present disclosure relates to a continuous production system and a diester-material production unit included therein, wherein the production unit includes a reaction device in which an esterification reaction of dicarboxylic acid and a primary alcohol is performed, a column in which gas-liquid separation of the primary alcohol and the water introduced is performed, a heat exchange device for recovering heat of a gas phase line of the column, a condenser installed at a rear end of the heat exchange device and liquefying a mixture of a gas-phase primary alcohol and water, and a layer separator in which the layer separation of a mixture of a liquefied primary alcohol and water is performed, wherein the heat exchange device includes one or more of a first heat exchanger for performing heat exchange with a raw material feed line of the reaction device, a second heat exchanger for performing heat exchange with a line through which a low temperature stream flows in a process, and a third heat exchanger for performing heat exchange with condensed water generated in the process. According to the present disclosure, the
(Continued)

amount of a coolant used and the volume of steam of a reactor may be reduced, and the thermal efficiency of the entire process may be improved.

11 Claims, 9 Drawing Sheets

(51) Int. Cl.
*B01D 19/00* (2006.01)
*B01J 19/00* (2006.01)
*B01J 19/24* (2006.01)
*C07C 67/475* (2006.01)
*C07C 67/52* (2006.01)
*C07C 69/82* (2006.01)

(52) U.S. Cl.
CPC ......... *B01J 19/0013* (2013.01); *B01J 19/245* (2013.01); *B01J 19/2465* (2013.01); *C07C 67/475* (2013.01); *C07C 67/52* (2013.01); *C07C 69/82* (2013.01); *B01J 2219/00033* (2013.01); *B01J 2219/00087* (2013.01); *B01J 2219/00108* (2013.01)

(58) Field of Classification Search
CPC ............ B01J 19/245; B01J 2219/00033; B01J 2219/00087; B01J 2219/0013; B01D 3/06; B01D 3/009
See application file for complete search history.

(56) References Cited

U.S. PATENT DOCUMENTS

| | | | |
|---|---|---|---|
| 6,173,585 | B1 | 1/2001 | Billy et al. |
| 2009/0264671 | A1* | 10/2009 | Noh ..................... C11C 1/005 560/129 |
| 2011/0269997 | A1 | 11/2011 | Cox et al. |
| 2015/0330706 | A1 | 11/2015 | Vermeiren et al. |
| 2017/0297998 | A1 | 10/2017 | Schraut et al. |
| 2019/0024971 | A1 | 1/2019 | Vermeiren et al. |
| 2019/0263745 | A1 | 8/2019 | Lee et al. |
| 2021/0040026 | A1 | 2/2021 | Lee et al. |

FOREIGN PATENT DOCUMENTS

| | | | | |
|---|---|---|---|---|
| JP | 2004-168978 | A | | 6/2004 |
| JP | 4158396 | B2 | | 10/2008 |
| KR | 10-1995-0005797 | A | | 3/1995 |
| KR | 950005797 | A | * 3/1995 | ............ C07C 67/39 |
| KR | 10-0122429 | B1 | | 11/1997 |
| KR | 10-2000-0006459 | A | | 1/2000 |
| KR | 10-0443389 | B1 | | 11/2004 |
| KR | 10-0806353 | B1 | | 2/2008 |
| KR | 10-2011-0047189 | A | | 5/2011 |
| KR | 10-2015-0095677 | A | | 8/2015 |
| KR | 10-1663586 | B1 | | 10/2016 |
| KR | 10-2018-0074984 | A | | 7/2018 |
| KR | 10-2019-0027622 | A | | 3/2019 |
| KR | 10-2019-0027623 | A | | 3/2019 |

* cited by examiner

DIESTER-BASED MATERIAL PRODUCTION UNIT AND DIESTER-BASED MATERIAL PRODUCTION SYSTEM INCLUDING THE SAME

CROSS-REFERENCE TO RELATED APPLICATIONS

This application is a National Phase entry pursuant to 35 U.S.C. § 371 of International Application No. PCT/KR2020/008674, filed on Jul. 2, 2020, and claims the benefit of and priority to Korean Patent Application No. 10-2019-0080462, filed on Jul. 4, 2019, in the Korean Intellectual Property Office, all of which are hereby incorporated by reference in their entirety for all purposes as if fully set forth herein.

TECHNICAL FIELD

The present invention relates to a diester-based material production unit with an improved heat exchange system and a diester-based material production system including the same.

BACKGROUND ART

Phthalate-based plasticizers had occupied 92% of the world's plasticizer market by the 20th century (Mustafizur Rahman and Christopher S. Brazel "The plasticizer market: an assessment of traditional plasticizers and research trends to meet new challenges" Progress in Polymer Science 2004, 29, 1223-1248), and are additives used to improve the processability of polyvinyl chloride (hereinafter, referred to as PVC) by imparting flexibility, durability, cold resistance, and the like and lowering viscosity during melting. Phthalate-based plasticizers are introduced into PVC in various contents and used not only for hard products such as rigid pipes, but also for soft products such as food packaging materials, blood bags, and flooring materials since the phthalate-based plasticizers are soft and stretchable. Thus, the phthalate-based plasticizers are more closely related to real life than any other materials and are widely used for materials which come into direct contact with a human body.

However, despite the compatibility with PVC and excellent softness imparting properties of phthalate-based plasticizers, there has been controversy over the harmful nature of the phthalate-based plasticizers in that when a PVC product containing a phthalate-based plasticizer is used in real life, the phthalate-based plasticizer may be leaked little by little out of the product and act as a suspected endocrine disruptor (environmental hormone) and a carcinogen to the level of a heavy metal (N R Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2008, 42, 7522-7527). Particularly, since a report was published in the 1960s in the United States that diethylhexyl phthalate (di-(2-ethylhexyl) phthalate, DEHP), the most used phthalate plasticizer, leaked out of PVC products, global environmental regulations have started to be implemented in addition to various studies on the harmful nature of the phthalate-based plasticizer on human bodies, boosted by increasing interest in environmental hormones in the 1990s.

Thus, in order to respond to environmental hormonal problems and environmental regulations due to the leakage of a phthalate-based plasticizer, di(2-ethylhexyl) phthalate in particular, many researchers have been conducting research in order to develop a new non-phthalate-based alternative plasticizer without phthalic anhydride used in the manufacturing of di(2-ethylhexyl) phthalate, and to develop a phthalate-based plasticizer which may replace di(2-ethylhexyl) phthalate and be used for industrial purposes since the leakage of the plasticizer is suppressed even though it is based on phthalate, as well as to develop a leakage suppression technology which suppresses the leakage of phthalate-based plasticizers, thereby significantly reducing risks to human bodies and which meets environmental standards.

As such, as diester-based plasticizers, the development of materials which are free from environmental problems and which may replace a di(2-ethylhexyl) phthalate having existing environmental problems is actively underway. In addition, research on developing a diester-based plasticizer with excellent physical properties as well as research on equipment for manufacturing the plasticizer have been actively conducted, and there has been a demand for more efficient, more economical and simpler process designs in terms of process design.

Meanwhile, a batch process is being applied in most industrial sites as a process of producing the above diester-based plasticizer. As the batch process, an invention related to a gas-liquid separation system for the reflux of non-reactants and efficient removal of sub-reactants in a reactor (Korean Patent Laid-Open Publication No. 10-2019-0027622) and an invention related to a system integrating facilities of a primary direct esterification reaction and a second trans-esterification reaction in order to simplify facilities of a batch process (Korean Patent Laid-Open Publication No. 10-2019-0027623) have been introduced. In the case of such a batch process, there is no proposed method for utilizing heat unnecessarily removed. This is due to the fact that heat flow is not constant due to the nature of the batch process. Due to the limitation, there has been a problem in that energy consumption is accumulated as the process proceeds.

In addition, as a continuous process, an invention related to a process configuring a reaction part by connecting two or more reactors in series (Korean Patent Publication No. 10-1663586) has also been introduced. However, there is no proposal of an alternative to the utilization of heat to be disposed of in the process.

PRIOR ART DOCUMENT

Patent Document (Patent Document 1) Korean Patent Laid-Open Publication No. 10-2019-0027622
(Patent Document 2) Korean Patent Laid-Open Publication No. 10-2019-0027623
(Patent Document 3) Korean Patent Laid-Open Publication No. 10-1663586

DISCLOSURE OF THE INVENTION

Technical Problem

An aspect of the present invention provides a diester-based material production system in which a heat exchange system is applied to a diester-based material production unit applied to a process of continuously producing a diester-based material, the heat exchange system being optimized through selecting a line to recover heat and a line to supply the recovered heat, so that the economic feasibility of the entire process may be significantly improved by reducing the amount of energy consumed for the production and raw materials of hot temperature water or steam or for preheating a low temperature stream injected into a purification tower and reducing the amount of a coolant required for condensation.

Technical Solution

According to an aspect of the present invention, there is provided a diester-based material production system including a production unit included in a continuous production system of a diester-based material, wherein the production unit includes a reaction device including a reaction vessel in which an esterification reaction of dicarboxylic acid and a primary alcohol is performed, a raw material feed line for supplying a reactant to the reaction vessel, and a gas phase discharge line installed at an upper end of the reaction vessel such that vaporized primary alcohol and water are discharged through a column, the column including a column main body in which gas-liquid separation of the primary alcohol and the water introduced from the gas phase discharge line is performed, a liquid phase line installed at a lower portion of the column main body such that a liquefied alcohol-rich stream flows into the reaction device, and a gas phase line installed at an upper portion of the column main body and connected to a layer separator such that a mixture stream of a gas-phase primary alcohol and water flows out, a heat exchange device installed on the gas phase line of the column and recovering heat of the gas phase line, a condenser installed on the gas phase line of the column and installed at a rear end of the heat exchange device and liquefying a mixture of the gas-phase primary alcohol and the water in the gas phase line, and the layer separator including a separation tank in which the layer separation of a mixture of the liquefied primary alcohol and the water into an organic layer and an aqueous layer is performed, an organic layer line installed to discharge the separated organic layer to a side upper portion of the column main body, and an aqueous line through which the separated aqueous layer is discharged.

The heat exchange device includes one or more among a first heat exchanger installed to transfer heat of the gas phase line of the column to the raw material feed line, a second heat exchanger installed to transfer the heat of the gas phase line of the column to a line through which a low temperature stream flows in the continuous production system of a diester-based material, and a third heat exchanger installed to transfer the heat of the gas phase line of the column to condensed water generated in the continuous production system of a diester-based material.

According to another aspect of the present invention, there is provided a method for continuously producing a diester-based material, the method is performed by a continuous production system of a diester-based material, comprising: a first reaction part in which a direct esterification reaction is performed, a first purification unit in which a product of the first reaction part is purified, a second reaction part in which a trans-esterification reaction is performed by introducing the purified product of the first reaction part and an alcohol different from a raw material alcohol of the first reaction part, and a second purification unit in which a product of the second reaction part is purified, wherein the first reaction part includes two or more production units connected in series. In the production unit, a process is performed which includes a step in which a primary alcohol, which is a non-reactant, and water, which is a side-reactant are vaporized by the esterification reaction of dicarboxylic acid and a primary alcohol in a reaction device, a step in which the vaporized primary alcohol and water ascends from a lower portion and a liquid-phase primary alcohol descends from an upper portion to be subjected to gas-liquid separation in a column and a gas-phase primary alcohol and water are discharged through an upper portion of the column, a step of recovering heat of the gas-phase primary alcohol and water, and a step of condensing the primary alcohol and water from which the heat has been recovered to be subjected to layer separation.

The recovered heat is applied to one or more uses of heating the dicarboxylic acid and the primary alcohol before being injected into the reaction device, heating one or more lines selected from the group consisting of a feed line of a purification tower included in the first purification unit, a raw material feed line of the second reaction part, and a feed line of a purification tower included in the second purification unit, and heating condensed water generated in the process.

According to yet another aspect of the present invention, there is provided a continuous production system of a diester-based material, the system including a first reaction part in which a direct esterification reaction is performed, a first purification unit in which a product of the first reaction part is purified, a second reaction part in which a trans-esterification reaction is performed by introducing the purified product of the first reaction part and an alcohol different from a raw material alcohol of the first reaction part, and a second purification unit in which a product of the second reaction part is purified, wherein the heat exchange device includes one or more among a first heat exchanger installed to transfer heat to a raw material feed line, a second heat exchanger installed to transfer the heat of the gas phase line of the column to one or more lines selected from the group consisting of a feed line of a purification tower included in the first purification unit, a raw material feed line of the second reaction part, and a feed line of a purification tower included in the second purification unit, and a third heat exchanger installed to transfer the heat of the gas phase line of the column to condensed water generated in the process.

Advantageous Effects

The present invention employs an improved heat exchange system, so that the economic feasibility of the entire process may be significantly improved by reducing the amount of energy consumed for the production and raw materials of hot temperature water or for preheating a low temperature stream and reducing the amount of a coolant required for condensation.

MODE FOR CARRYING OUT THE INVENTION

Figure 1:
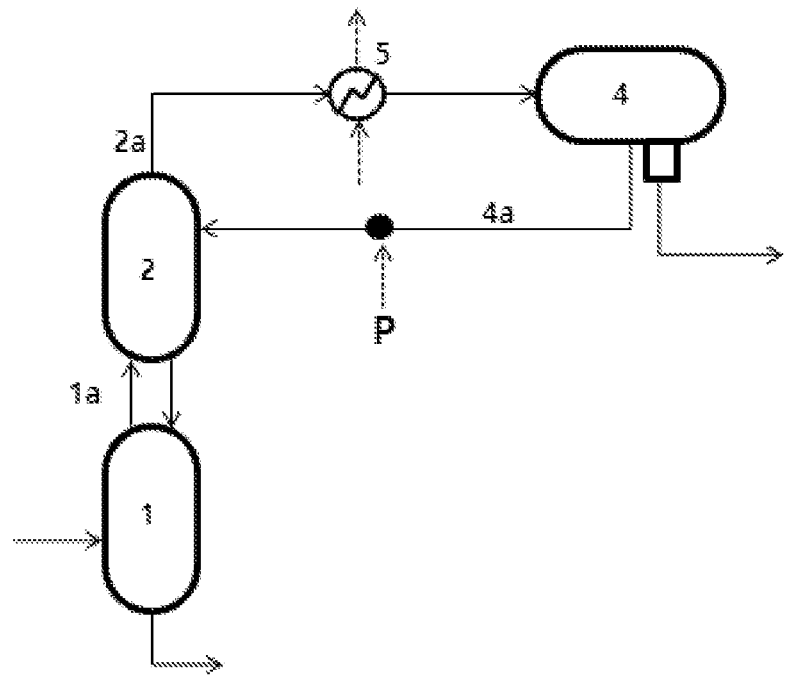
FIG. 1 is a process diagram showing a typical diester-based material production process.

Hereinafter, the present invention will be described in more detail to facilitate understanding of the present invention.

It will be understood that words or terms used in the description and claims of the present invention shall not be construed as being limited to having the meaning defined in commonly used dictionaries. It will be further understood that the words or terms should be interpreted as having meanings that are consistent with their meanings in the context of the relevant art and the technical idea of the invention, based on the principle that an inventor may properly define the meaning of the words or terms to best explain the invention.

A diester-based material production unit according to an embodiment of the present invention is included in a continuous production system of a diester-based material and includes a reaction device including a reaction vessel in which an esterification reaction of dicarboxylic acid and a primary alcohol is performed, a raw material feed line for supplying a reactant to the reaction vessel, and a gas phase discharge line installed at an upper end of the reaction vessel such that vaporized primary alcohol and water are discharged through a column, the column including a column main body in which gas-liquid separation of the primary alcohol and the water introduced from the gas phase discharge line is performed, a liquid phase line installed at a lower portion of the column main body such that a liquefied alcohol-rich stream flows into the reaction device, and a gas phase line installed at an upper portion of the column main body and connected to a layer separator such that a mixture stream of a gas-phase primary alcohol and water flows out, a heat exchange device installed on the gas phase line of the column and recovering heat of the gas phase line, a condenser installed on the gas phase line of the column and installed at a rear end of the heat exchange device and liquefying a mixture of the gas-phase primary alcohol and the water in the gas phase line, and the layer separator including a separation tank in which the layer separation of a mixture of the liquefied primary alcohol and the water into an organic layer and an aqueous layer is performed, an organic layer line installed to discharge the separated organic layer to a side upper portion of the column main body, and an aqueous line through which the separated aqueous layer is discharged.

The heat exchange device includes one or more among a first heat exchanger installed to transfer heat of the gas phase line of the column to the raw material feed line, a second heat exchanger installed to transfer the heat of the gas phase line of the column to a line through which a low temperature stream flows in the continuous production system of a diester-based material, and a third heat exchanger installed to transfer the heat of the gas phase line of the column to heat condensed water generated in the continuous production system of a diester-based material.

FIG. 1 shows a process diagram applied to a typical production process for a diester-based material. In a reaction device 1, an esterification reaction is performed, and simultaneously, an alcohol and water are vaporized, and then injected into a column 2 through a gas phase discharge line 1*a*, and in the column 2, a gas-phase alcohol and water come in contact with a liquid-phase alcohol supplied by an organic layer line 4*a* and refluxed from a layer separator 4, and thus, gas-liquid separation is performed. A gas-phase water and alcohol not separated are discharged through a gas phase line 2*a* of the column, and then sent back to the reaction device 1 through layer separation in the layer separator 4 after being subjected to cooling and condensation by a condenser 3 installed on the gas phase line 2*a*, but refluxed to an upper portion of the column 2 for the gas-liquid separation in the column 2.

Figure 2:
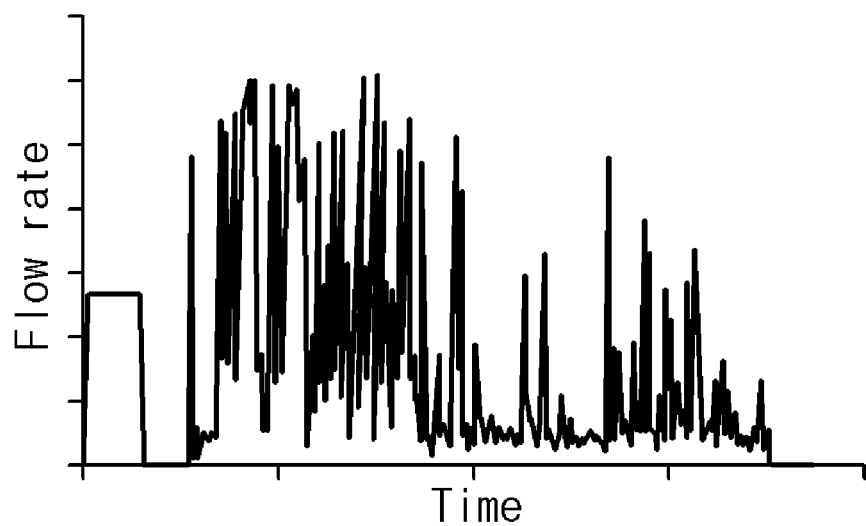
FIG. 2 is a reflux line recovered to a column in a batch process, and is a graph showing a heat flow rate over time at a position P of FIG. 1.

Meanwhile, looking at the heat flow rate of a stream in the organic layer line 4*a*, the range of change thereof is quite wide as shown in the graph of FIG. 2 showing the heat flow rate over time at the position P of the organic layer line 4*a* illustrated in FIG. Therefore, it is not a system capable of recovering heat typically, so that a system in which a total amount of heat present in the gas phase line 2*a* above the column 2 is disposed from a condenser is applied.

The diester-based material production unit according to an embodiment of the present invention is applied to a continuous process, and is designed to recover and utilize heat of a stream discharged from an upper portion of a column from the fact that the heat flow rate of refluxed stream in a line is constant. By applying such a heat exchange system, it is possible to expect an effect of increasing energy productivity through preheating of raw materials and/or producing hot temperature water or steam using condensed water in the process, and reducing the amount of a coolant used in the condenser at a rear end.

Hereinafter, the diester-based material production unit according to an embodiment of the present invention will be described with reference to the accompanying drawings.

Figure 3:
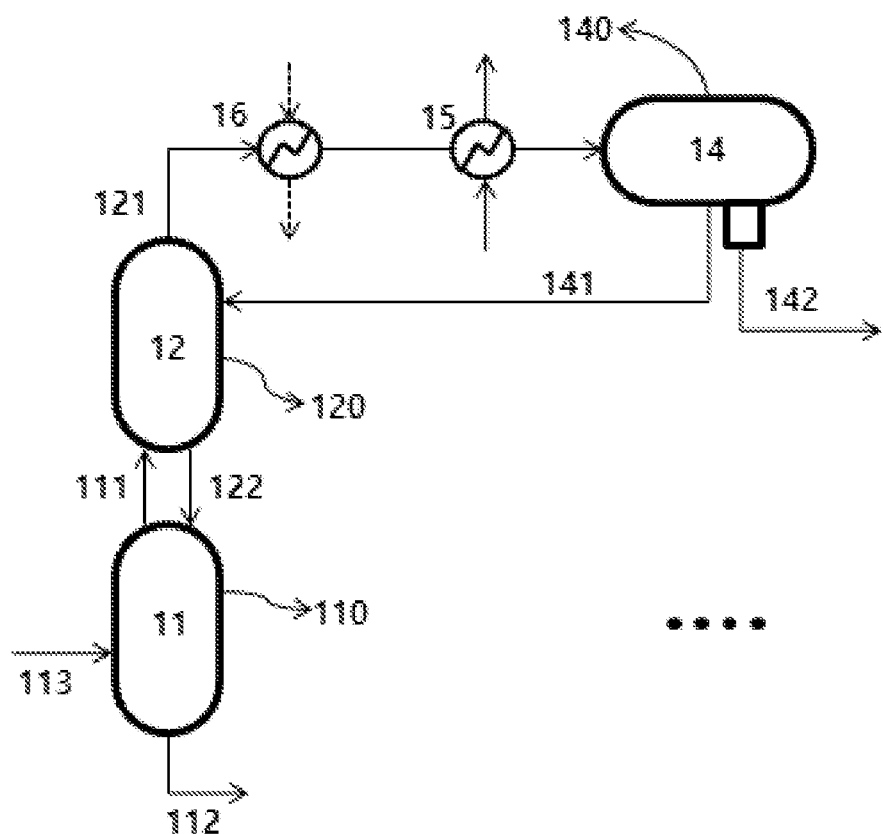
FIG. 3 is a process diagram showing a diester-based material production unit of according to an embodiment of the present invention.

FIG. 3 is a process diagram showing a production unit 10 of a diester-based material according to an embodiment of the present invention. A facility in which a diester-based material is produced includes a reaction device 11 in which an esterification reaction of dicarboxylic acid and a primary alcohol is performed, a column 12 in which gas-liquid separation is performed by pulling up an alcohol, which is a non-reactant vaporized during a reaction, and water, which is a side-reactant, a heat exchange device 16 for recovering heat of a gas phase line 121 discharged to an upper portion of the column, a condenser 15 for liquefying a mixture of a gas-phase primary alcohol and water before introducing the same into a layer separator, and a layer separator 14 for separating the mixture of the liquefied primary alcohol and the water through layer separation.

According to an embodiment of the present invention, the production unit 10 includes the reaction device 11, and the reaction device 11 includes a reaction vessel 110 in which an esterification reaction of dicarboxylic acid and a primary alcohol is performed, and a gas phase discharge line 111 installed at an upper end of the reaction vessel 110 through which vaporized primary alcohol and water are discharged to a column therethrough.

The reaction device 11 may also have a raw material feed line 113 through which dicarboxylic acid and a primary alcohol, which are raw materials, are injected, and a product line 112 for sending a product to a reaction device of the next production unit if a plurality of production units are provided, or to a purification unit when there is a single production unit or when it is the last production unit of a plurality of production units.

However, the raw material feed line 113 may have a pre-mixer (not shown) further installed at a front end of an initial production unit to inject raw materials into the pre-mixer, thereby supplying the raw materials to a reaction device, or may supply raw materials by performing line mixing with one raw material feed line. Alternatively, raw materials may be supplied through different feed lines for each raw material. The feed method of raw materials is not particularly limited as long as it is a method capable of supplying raw materials into a reaction device.

In addition, the production unit 10 includes the column 12, and the column 12 connected to the reaction device 11 through the gas phase discharge line 111 includes a column main body 120 in which gas-liquid separation of the primary alcohol and the water introduced from the gas phase discharge line 111 is performed, a liquid phase line 122 installed at a lower portion of the column main body 120 such that a liquefied alcohol-rich stream flows into the reaction device, and a gas phase line 121 installed at an upper portion of the column main body 120 and connected to the layer separator 14 such that a mixture stream of the gas-phase primary alcohol and the water flows out.

In the reaction device 11, an esterification reaction is performed in the reaction vessel 110, and the reaction may be performed at a temperature of about 150° C. to 230° C. by having dicarboxylic acid and a primary alcohol as raw materials. The dicarboxylic acid, which is a raw material, may include one or more selected from the group consisting of terephthalic acid, phthalic acid, isophthalic acid, and cyclohexane dicarboxylic acid, and the primary alcohol which is another raw material may have 3 to 10 carbon atoms.

When the raw materials are used to perform an esterification reaction, the reaction temperature of the esterification reaction may be higher than the boiling point of the primary alcohol having 3 to 10 carbon atoms applied as a raw material, so that the vaporization of the primary alcohol inevitably occurs during the reaction. In addition, due to the evaporation of the primary alcohol, a problem in which reactants are continuously decreased in a reaction vessel occurs. Therefore, the reaction is performed by injecting an excess amount of the primary alcohol above an equivalent ratio in theory.

Accordingly, the molar ratio of the dicarboxylic acid and the primary alcohol in a reaction part (particularly, a first reaction part in a production system to be described later) may be 1:2 to 1:5, and may be to prevent energy loss due to unnecessary reflux caused by the feed of an excessive amount of alcohol and may be determined in consideration of the excess amount of alcohol required in terms of achieving the conversion rate of the reaction and controlling the minimum residence time. The molar ratio may preferably be 1:2 to 1:4, and in order to optimally reflect the above, a molar ratio of 1:2.5 to 1:4 may be applied.

In addition, the esterification reaction generates water as a side-reactant, but the generation of water, on the contrary, may accelerate a reverse reaction and become the cause to interfere with the achievement of a target conversion rate, and thus, it may also be important to remove the water from a reaction vessel.

That is, gas-phase water generated during the reaction should be removed in the reaction device 11, and inevitably, the operation to re-liquefy the vaporized primary alcohol and return the re-liquefied primary alcohol to the reactor is essential. Accordingly, the column 12 is installed at an upper portion of the reaction device 11.

In the column 12, the gas-liquid separation of the vaporized primary alcohol and the water is performed. The mixture of the gas-phase primary alcohol and the water is introduced to a lower portion of the column main body 120 of the column 12 from the gas phase discharge line 111 at the upper portion of the reaction vessel 110, and the introduced gas-phase mixture ascends in the column main body 120 of the column 12 and comes in contact with a liquid-phase primary alcohol descending from a side upper portion of the column 12, so that the primary alcohol and the water are separated into the lower portion of the column main body 120 and the upper portion of the column main body 120, respectively. Here, the liquid-phase primary alcohol descending from an upper portion of the column 12 may be supplied from the layer separator 14 at a rear end.

The primary alcohol and the water vaporized in the reaction device 11 are primarily separated through the gas-liquid separation in the column 12, and the liquefied primary alcohol is supplied back to the reactor 110 through the liquid phase line 122, and thus, may participate in the reaction. In addition, a mixture gas of water still in gas phase and unseparated primary alcohol is discharged through the gas phase line 121 at the upper portion of the column. At this time, the temperature of an internal gas phase mixture stream discharged through the gas phase line 121 may be about 130° C. to 180° C. Although a portion of the primary alcohol is liquefied and returned to the reactor, the primary alcohol may still be excessive, and thus, the weight ratio of the primary alcohol to the water may be about 1 or more.

According to an embodiment of the inventive concept, the production unit 10 includes the heat exchange device 16 for recovering the heat of the gas phase line 121 of the column and transferring the same to another place which needs heat supply in the process, and the heat exchange device 16 is installed on the gas phase line 121 of the column 12.

The mixture stream of the gas-phase water and primary alcohol discharged through the gas phase line 121 from the column should be eventually liquefied such that the primary alcohol is refluxed and the water is removed, which is a stream from which heat should be removed. In addition, since the gas line 121 is a fairly high-temperature stream at about 130° C. to 180° C., and thus disposing the heat embedded therein may result in significant energy loss.

However, in a typical batch process, due to the problem in that the heat flow rate is not constant, heat was removed only with a condenser, and thus, there is significant energy loss. Even for a continuous process, there has been no proposal for the selection or utilization of a line capable of recovering and supplying heat.

Accordingly, the present invention is characterized by having a heat exchange system in which disposed heat is recovered and supplied to an appropriate position in order to increase the efficiency of energy utilization. Specifically, the heat exchange device 16 of the present invention is to recover heat from the gas phase line 121 installed at an upper portion of the column 12 as described above, and the recovered heat is supplied to the raw material feed line 113 of the reaction device 11, supplied to a line through which a low temperature steam flows in a process (a production system to be described later), or used to heat condensate generated in the process (the production system to be described later) to produce high temperature water or steam.

Specifically, the continuous production system of a diester-based material including the production unit of the present invention may include a first reaction part in which a direct esterification reaction is performed, a first purification unit in which a product of the first reaction part is purified, a second reaction part in which a trans-esterification reaction is performed by introducing the purified product of the first reaction part and an alcohol different from a raw material alcohol of the first reaction part, and a second purification unit in which a product of the second reaction part is purified.

In this case, the heat exchange device installed on the gas phase line of the upper portion of the column may be installed for the heat exchange with a low temperature stream in the production system, and the low temperature stream may be feed lines of purification towers present in the first purification unit and the second purification unit or a raw material feed line of the second reaction part, and the heat exchange device may be installed to supply heat to the lines. In the case of the purification towers provided in the first purification unit and the second purification unit, it is common that a stream injected into the purification tower is at a low temperature and the inside of the tower is heated for purification, and thus, when heat is supplied through the above feed line, the thermal efficiency of the entire process may be improved.

In addition, as described above, when such a heat exchange system is applied to heat exchange with a raw material feed in a production unit and/or to the production of a utility (hot temperature water or steam) in a production system, the productivity of the utility (hot temperature water or steam) may be improved, the amount of a coolant required for condensation, which is essentially performed at a rear end, may be reduced, and the energy efficiency of the entire process may be increased in terms of utilizing disposed heat.

The production unit 10 includes the layer separator 14. The layer separator 14 connected to the column 12 through the column gas phase line 121 includes a separation tank 140 in which a gas phase discharged from the upper portion of the column 12 and then liquefied via the heat exchange device 16 and the condenser 15 is subjected to layer separation into an organic layer and an aqueous layer, an organic layer line 141 from which the separated organic layer is discharged, and an aqueous layer line 142 from which the separated aqueous layer is discharged.

Furthermore, the production unit 10 includes a condenser 15 for performing cooling and condensing such that a stream in the gas phase line 121 at the upper portion of the column via the heat exchanger 16 may be all liquefied before being introduced into the layer separator 14, and the condenser 15 is installed on the gas phase line 121 of the column 12, and installed at a rear end of the heat exchange device 16 such that a stream in the line from which heat is sufficiently recovered by the heat exchange device 16 is cooled and condensed. The liquefied liquid-phase primary alcohol and water are separated into an organic layer of the primary alcohol and an aqueous layer of the water in the separation tank 140 of the layer separator 14.

The primary alcohol in the organic layer may be recirculated to the column 12 through the organic layer line 141, and may be injected into a side upper portion of the column main body 120 such that gas-liquid separation is performed in the column 12. At this time, the temperature of a primary alcohol stream in the organic layer line may be about 40° C. to about 95° C. In a typical batch process, a heat flow rate in the organic layer line is not constant. However, in a continuous process, the heat flow rate is stable, and thus, heat exchange may be possible in the gas phase line 121 at the upper portion of the column.

In addition, the water in the aqueous layer is discharged from the separation tank 14 through the aqueous layer line 142. At this time, the discharged water may be used to produce steam through an additional separation facility as generated water in the process, and there is no particular limitation to the utilization of the water after being removed from the reaction device 11.

Figure 4:
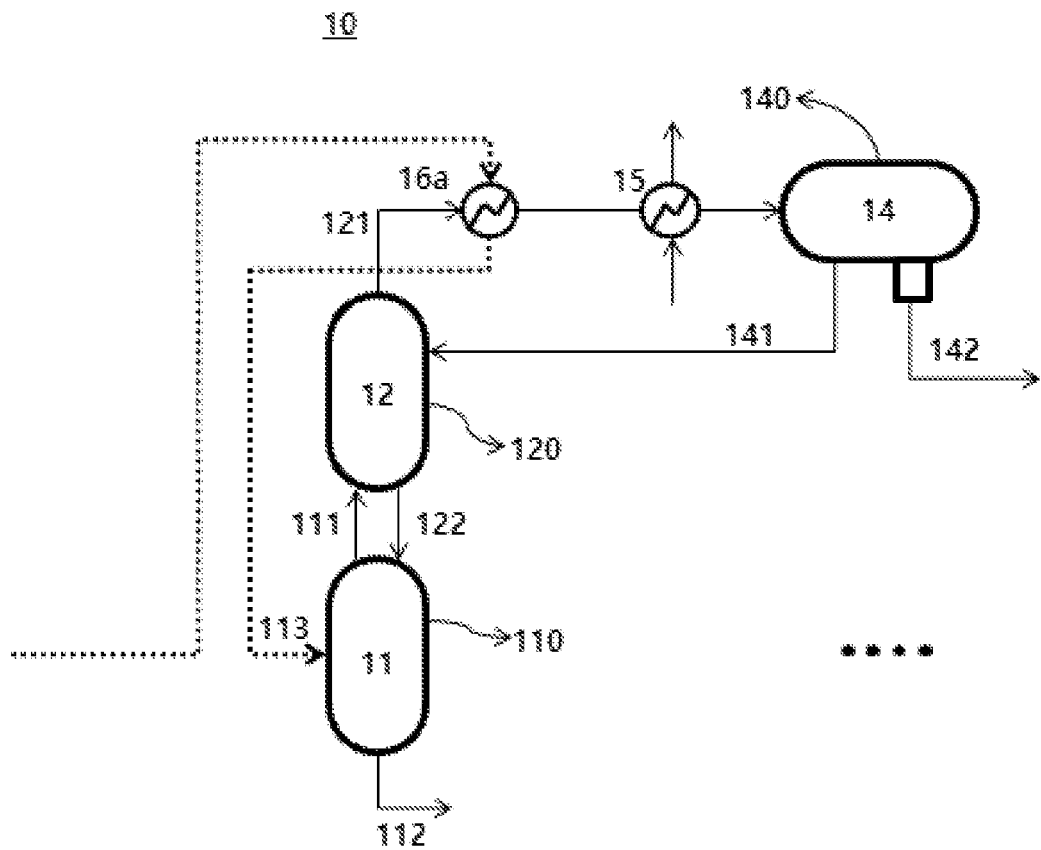
FIG. 4 is a process diagram showing an example of a heat exchange device (a first heat exchanger) as a production unit for a diester-based material according to an embodiment of the present invention.
Figure 5:
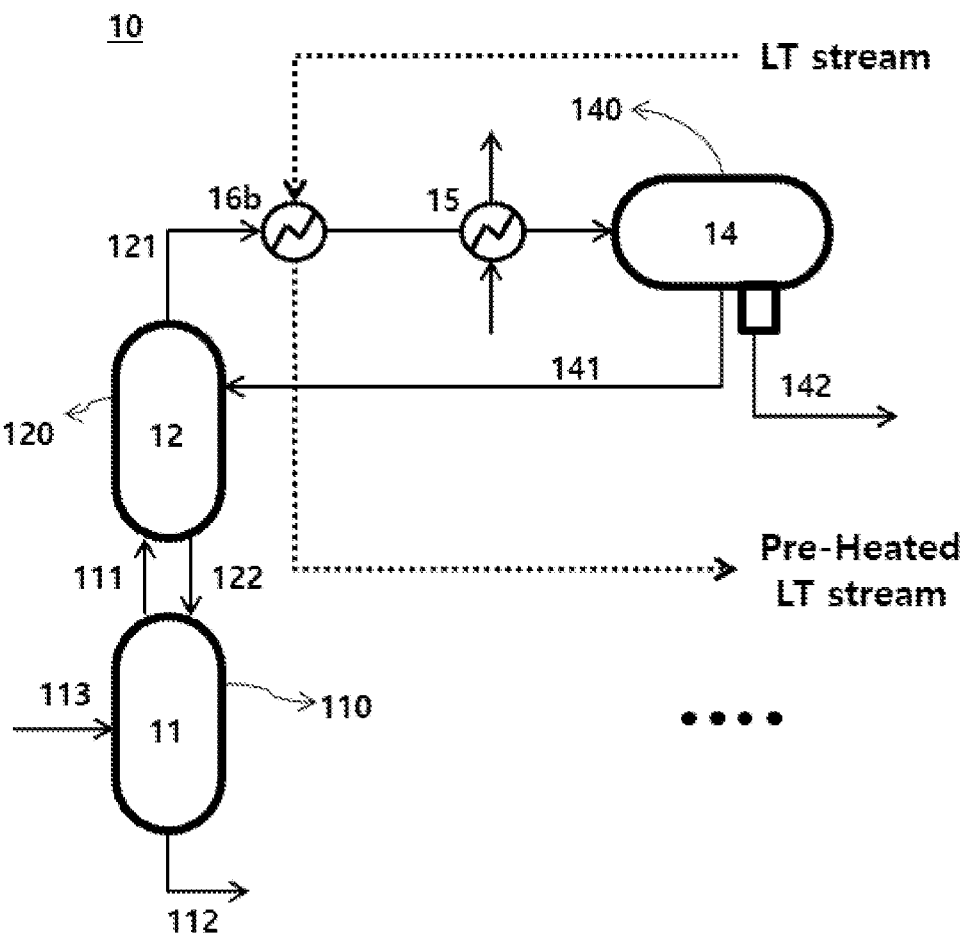
FIG. 5 is a process diagram showing an example of a heat exchange device (a second heat exchanger) as a production unit for a diester-based material according to an embodiment of the present invention.
Figure 6:
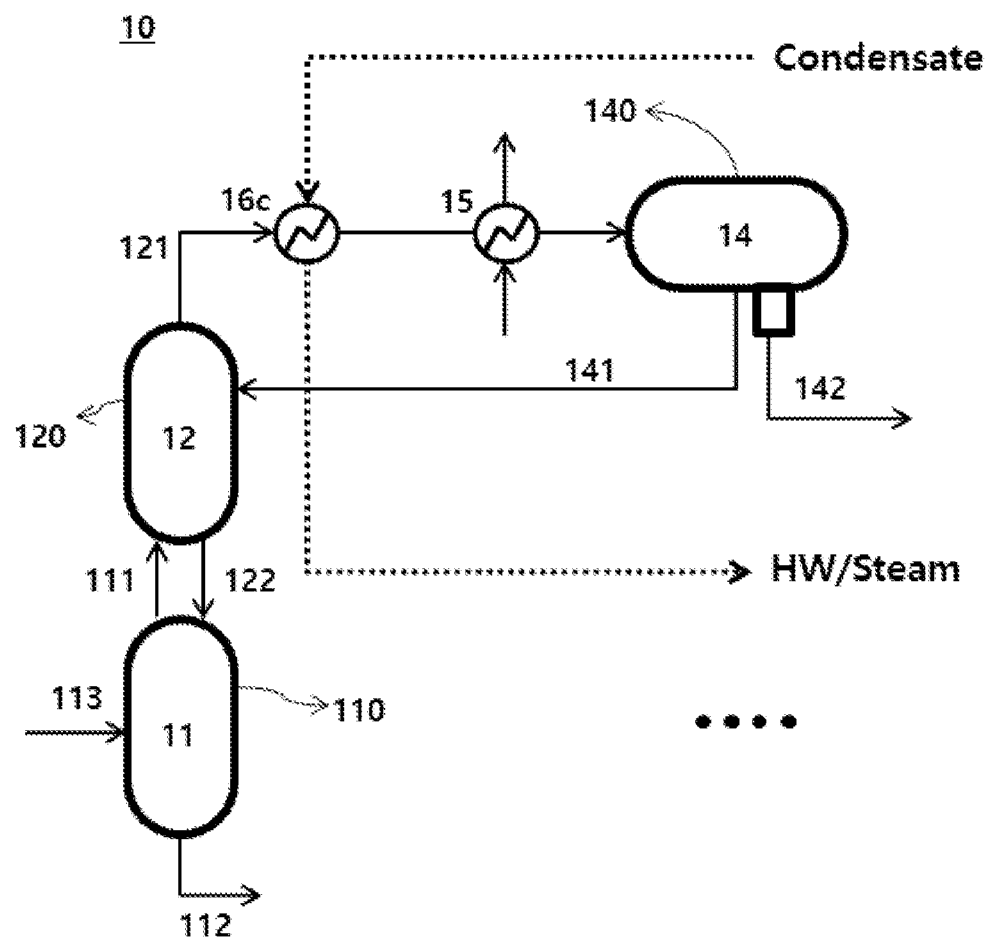
FIG. 6 is a process diagram showing an example of a heat exchange device (a third heat exchanger) as a production unit for a diester-based material according to an embodiment of the present invention.

FIGS. 4 to 6 show an example of a diester-based material production unit according to an embodiment of the present invention, and show an example of a manner in which a heat exchange system is applied.

Referring to FIG. 4, an example of a heat exchange system will be described. Here, a heat exchange device is installed to include a first heat exchanger 16a, and may be installed to transfer heat of the gas phase line 121 of the column 12 to the raw material feed line 113. The raw material feed line 113 may not be directly connected to the reaction vessel 110, but may be installed via the reaction vessel 110 to cross each other in the heat exchange device installed on the gas phase line 121 of the column 12. In this case, heat is removed from the gas phase line 121 to be condensed, so that the amount of a coolant in the condenser 15 at a rear end may be reduced, and a raw material may be pre-heated to a predetermined temperature before being injected into a reaction system in which a reaction is performed at about 150° C. to 230° C., so that the volume of steam used in a reactor may also be reduced.

Referring to FIG. 5, another example of a heat exchange system will be described. Here, a heat exchange device is installed to include a second heat exchanger 16b, and may be installed to transfer heat of the gas phase line 121 of the column 12 to another line in a process (production system). That is, the heat may be transferred to a low temperature stream LT stream in the production system. Here, the low temperature stream may have a feed line injected into a purification tower present in each of a first purification unit and a second purification unit, and a raw material feed line of a second reaction part.

Referring to FIG. 6, yet another example of a heat exchange system will be described. Here, a heat exchange device is installed to include a third heat exchanger 16c, and may be installed to transfer heat to use the heat of the gas phase line 121 of the column 12 for heating condensated water or condensates generated in a process.

The entire production process of a diester-based material requires a significant amount of utility (a heating source such as high temperature water HW or steam) such as steam for heating the reaction vessel 11, steam for heating to a specific temperature before injecting into a column in a purification process, and high temperature water to heat up to a required temperature in a neutralization process. In addition, in the production process, a considerable amount of condensate may be generated such as reaction product water of an aqueous layer generated from the layer separator 14 described above, or wastewater generated from the purification process. Therefore, a large amount of condensate generated in the process may be allowed to pass through the heat exchange device 16 to be utilized to produce the high temperature water HW or steam, thereby playing a big role in reducing the amount of condensate waste and improving the productivity of the utility in the process.

Figure 7:
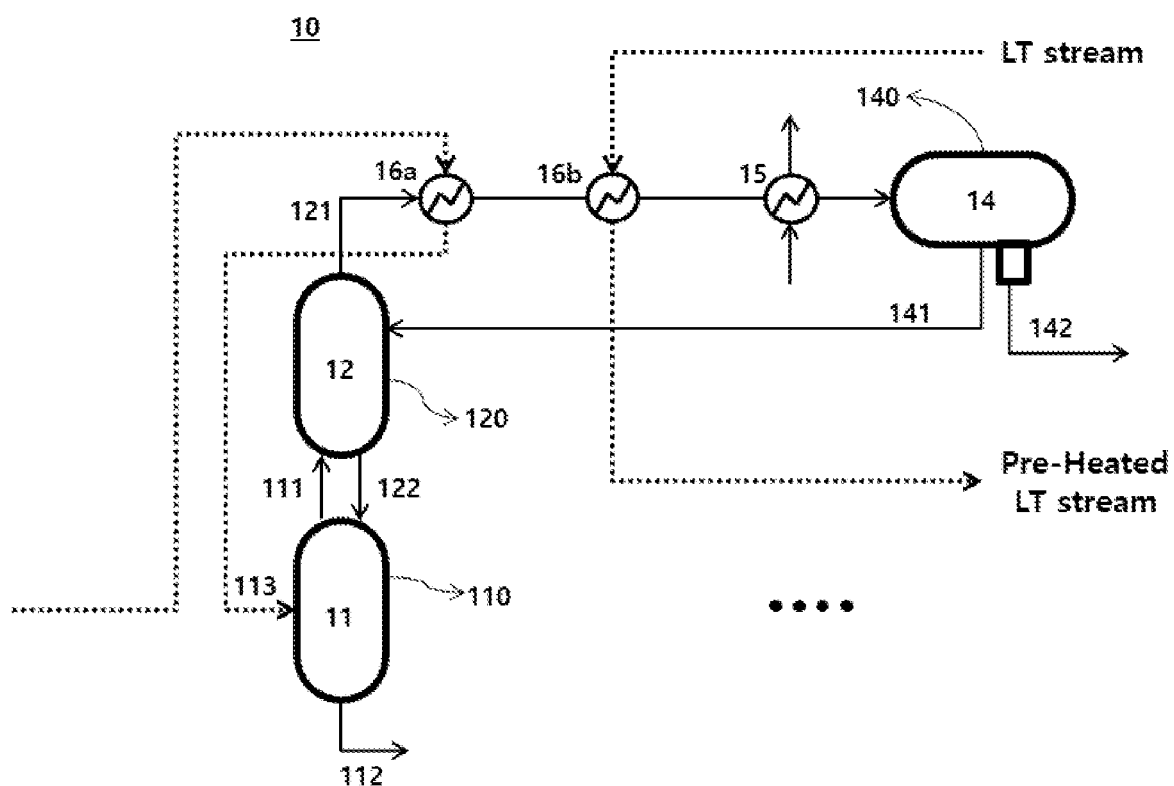
FIG. 7 is a process diagram showing an example of a heat exchange device (a first heat exchanger and a second heat exchanger) as a production unit for a diester-based material according to an embodiment of the present invention.
Figure 8:
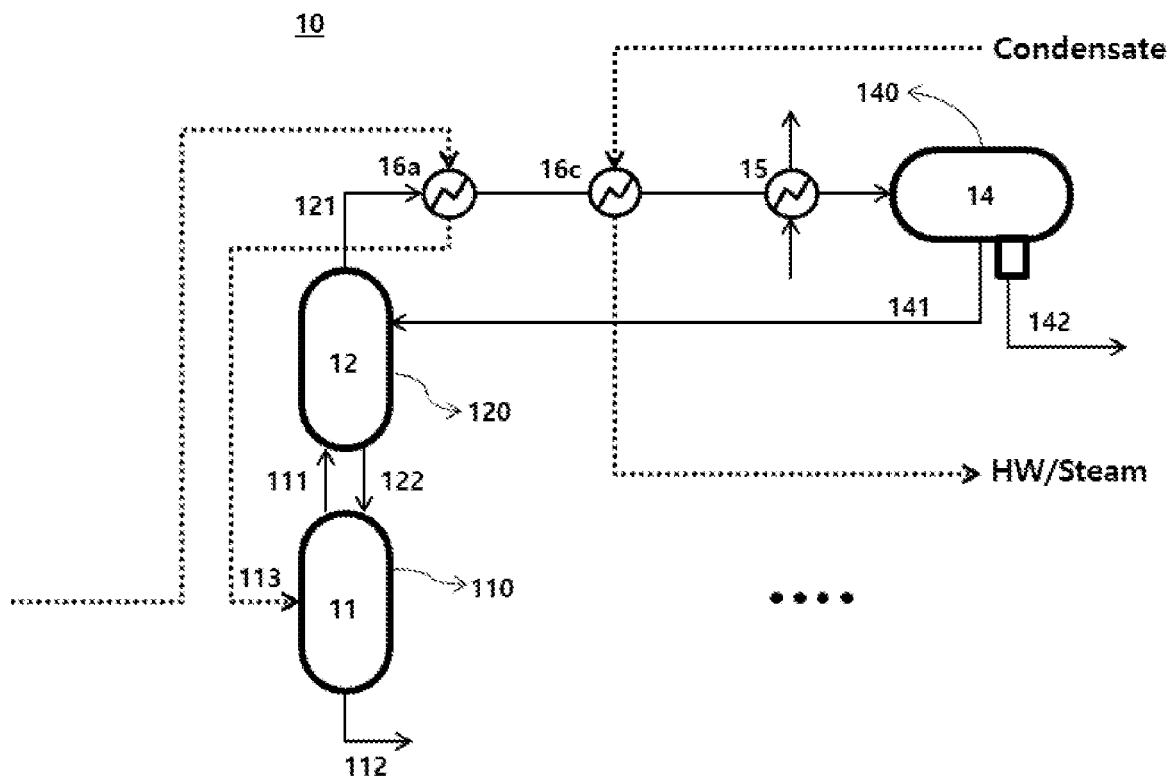
FIG. 8 is a process diagram showing an example of a heat exchange device (a first heat exchanger and a third heat exchanger) as a production unit for a diester-based material according to an embodiment of the present invention.
Figure 9:
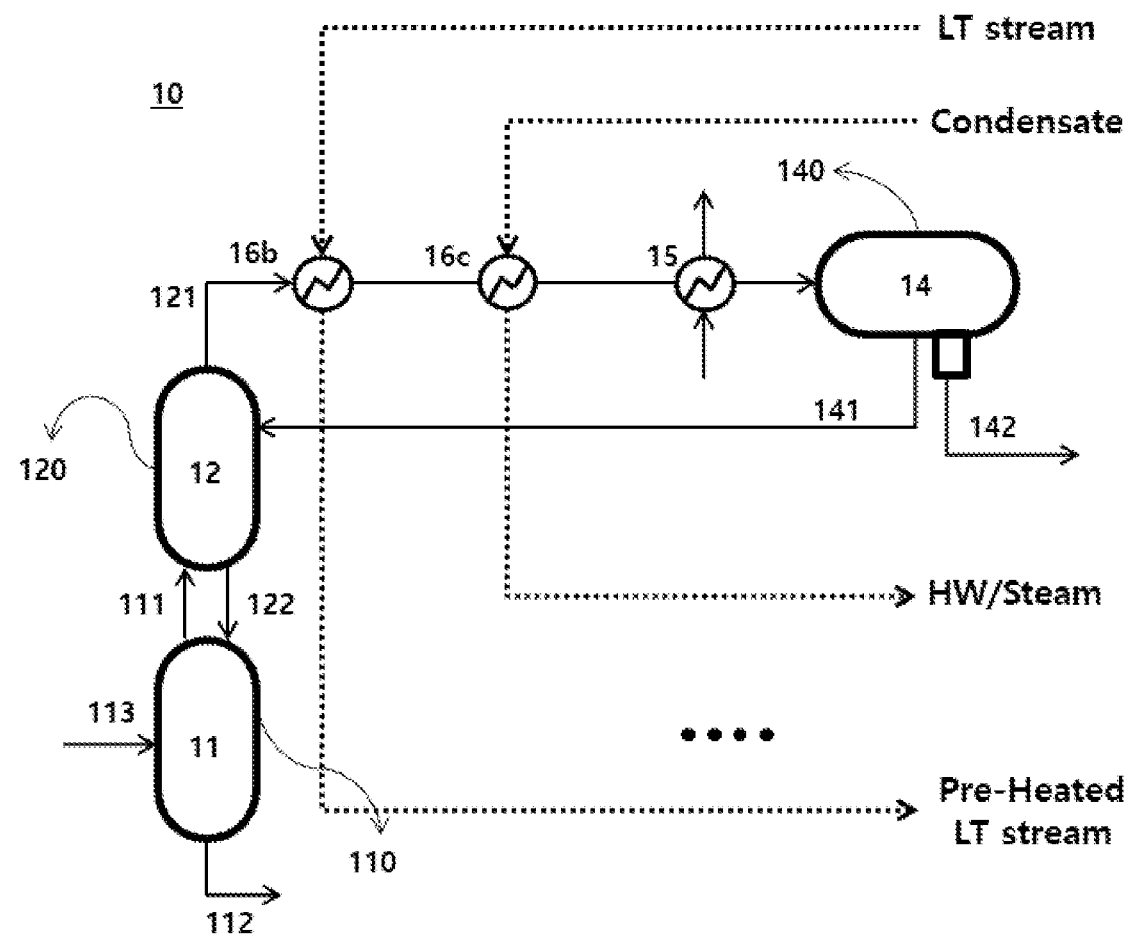
FIG. 9 is a process diagram showing an example of a heat exchange device (a second heat exchanger and a third heat exchanger) as a production unit for a diester-based material according to an embodiment of the present invention.

FIGS. 7 to 9 show other examples of a heat exchange system. Here, the heat exchange devices 16a, 16b, and 16c may be ones to which a composite system of the heat exchange system illustrated in FIGS. 4 to 6 is applied. In other words, as two heat exchangers, the first heat exchanger 16a installed to transfer heat of the gas phase line 121 of the column to the raw material feed line 113 with, the second heat exchanger 16b installed to transfer the heat to a low temperature stream in a production system, and the third heat exchanger 16c installed to transfer the heat of the gas phase line 121 of the column to produce a utility, such as heating condensate generated in the production system (process).

In this case, the amount of heat which may be recovered from the gas phase line 121 of the column and supplied to the raw material input line 113 and the amount which may be used for the production of the low temperature stream and the utility in the production system may be appropriately adjusted. The order of the first heat exchanger 16a, the second heat exchanger 16b, and the third heat exchanger 16c may be irrelevant.

However, for example, as in the cases of installing the second heat exchanger 16b at a rear end of the first heat exchanger 16a (see FIG. 7), installing the third heat exchanger 16c at a rear end of the first heat exchanger 16a (see FIG. 8), and installing the third heat exchanger 16c at a rear end of the second heat exchanger 16b (see FIG. 9), in terms of the overall heat exchange efficiency, it may be preferable to apply the heat exchange system in the order of preheating a raw material, performing heat exchange with a low temperature stream, and producing a utility.

As described above, when the diester-based material production unit to which the heat exchange system according to an embodiment of the present invention is applied to a production process, the utility utilization in the overall process may be increased, and the efficiency of energy use may be greatly improved.

According to another embodiment of the present invention, the production unit 20 may include, at a rear end of the heat exchange device, a flash drum having a flash drum main body in which separation of a liquid phase and a gas phase is performed in the mixture stream including the primary alcohol and the water, a flash drum lower line installed to discharge the liquid phase including a liquefied primary alcohol to the column or the reaction device, and a flash drum upper line installed to discharge the mixture stream of the gas-phase primary alcohol and the water to the layer separator. In this case, the gas phase line of the column may be connected to a side portion of the flash drum main body, and the condenser may be installed on the flash drum upper line.

When the flash drum is introduced into the production unit as described above, a liquid phase obtained by a portion of a gas phase condensed while passing through the heat exchanger and present in a line may be easily separated without any special operation, and an alcohol refluxed through the flash drum has a relatively high temperature, so that an effect of further improving the thermal efficiency of a reaction system may be expected.

Figure 10:
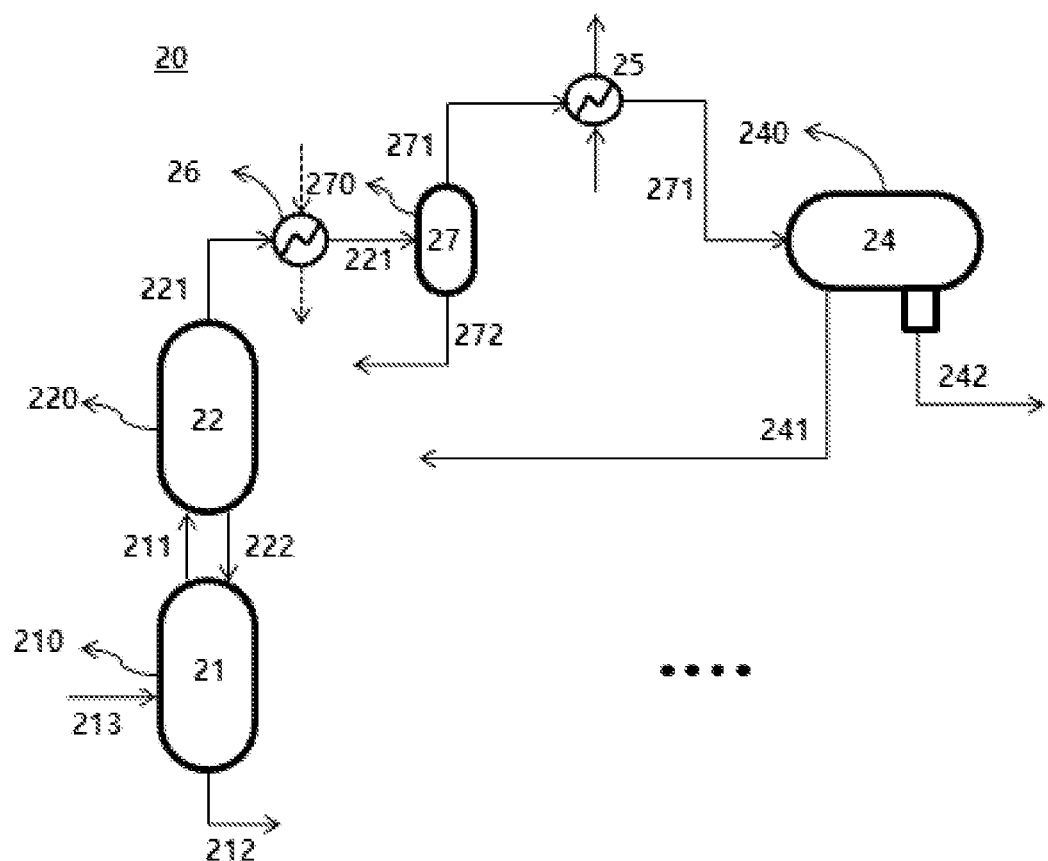
FIG. 10 is a process diagram showing a diester-based material production unit according to another embodiment of the present invention.

FIG. 10 shows the production unit 20 according to another embodiment of the present invention in which a flash drum is introduced. The flash drum 27 is connected to the column 22 through the gas phase line 221 and may have a flash drum main body 270 in which the mixture stream including partially liquefied primary alcohol and water by the heat exchange device 26 is subjected to gas-liquid separation, a flash drum lower line 272 through which a liquid phase including the liquefied primary alcohol is discharged, and a flash drum upper line 271 installed to discharge a mixture stream of the gas-phase primary alcohol and the water to the layer separator 24. At this time, a condenser 25 may be installed on a flash drum upper line 271.

The flash drum 27 may perform the gas-liquid separation inside the flash drum main body 270, and may return a large amount of primary alcohol to the reactor through simple equipment and treatment. At this time, the liquefied primary alcohol may be recovered to the reaction system through the reaction device 21 or the column 22 through the flash drum lower line 272. Since the temperature of the primary alcohol recovered from the flash drum 27 is higher than that by condensation and cooling, even if the primary alcohol is recovered to the reaction device 21, it is possible to minimize the temperature change in the reaction system. Also, since a portion of the primary alcohol is primarily separated, the amount of cooling water used in the condenser may be reduced, and thus, the energy saving effect obtained through the introduction of the flash drum 27 may be significant.

The production unit 20 according to another embodiment of the present invention includes a flash drum lower line 272 of the flash drum 27 and the organic layer line 241 of the layer separator 24 as lines for subjecting a primary alcohol to reflux, that is, recirculation. In returning the primary alcohol to the reaction device 21, the recirculation lines may be connected at various positions. The flash drum lower line 272 is connected to one or more positions selected from the group consisting of a side upper portion of the column main body 220, a side lower portion of the column main body 220, and the reaction vessel 210, and the organic layer line 241 is connected to one or more positions selected from the group consisting of a side portion of the flash drum main body 270, the side upper portion of the column body main 220, the side lower portion of the column main body 220, and a reaction vessel 210.

At this time, any one of the flash drum lower line 272 and the organic layer line 241 is necessarily to be connected to the side upper portion of the column main body 220 of the column 22. This is because gas-liquid separation may be performed only when a gas phase ascends in a lower portion and a liquid phase descends in an upper portion of the column main body 220 of the column 22.

A diester-based material production system according to another embodiment of the present invention may include a first reaction part in which a direct esterification reaction is performed, a first purification unit in which a product of the first reaction part is purified, a second reaction part in which a trans-esterification reaction is performed by introducing the purified product of the first reaction part and an alcohol different from a raw material alcohol of the first reaction part, and a second purification unit in which a product of the second reaction part is purified, wherein the first reaction part includes two or more of the above-described production unit connected in series.

In addition, the heat exchange device includes one or more among a first heat exchanger installed to transfer heat to a raw material feed line, a second heat exchanger installed to transfer the heat of the gas phase line of the column to one or more lines selected from the group consisting of a feed line of a purification tower included in the first purification unit, a raw material feed line of the second reaction part, and a feed line of a purification tower included in the second purification unit, and a third heat exchanger installed to transfer the heat of the gas phase line of the column to condensed water generated in the process (production system).

The above-described production unit of a diester-based material may be one unit constituting a portion of the 'reaction part' in view of the entire process. In the present invention, in a continuous process of producing a diester-based material, it is preferable that two or more of such production units are connected, preferably 3 to 6 or 3 to 5.

When two or more of the production units 10 and 20 are connected, a product produced in the reaction devices 11 and 12 may be discharged through the product lines 112 and 212 and moved to the next production unit. " . . . " represented in the accompanying drawings may be interpreted as an expression that two or more production units may be coupled.

Specifically, the continuous process of producing a diester-based material may include a first production system including a first reaction part in which a direct esterification reaction is performed and a first purification unit in which a product of the first reaction part is purified, and a second production system including a second reaction part in which a trans-esterification reaction with a diester generated through an additional feed of alcohol is performed and a second purification unit in which a product of the second reaction part is purified. Furthermore, a wastewater treatment unit or a mixed alcohol separation unit may be included.

The production unit according to an embodiment of the present invention may particularly relate to the first reaction part in the first production system in which a direct esterification reaction is performed. However, even if the first purification unit, the second reaction unit, and the second purification unit at a rear end are not connected together, a process is not particularly limited as long as it is a process to which a heat exchange system same as the one applied to the production unit according to the present invention may be applied.

A method for continuously producing a diester-based material according to another aspect of the present invention includes a first reaction part in which a direct esterification reaction is performed, a first purification unit in which a product of the first reaction part is purified, a second reaction part in which a trans-esterification reaction is performed by introducing the purified product of the first reaction part and an alcohol different from a raw material alcohol of the first reaction part, and a second purification unit in which a product of the second reaction part is purified, wherein the first reaction part includes two or more production units connected in series. In the production unit, a process is performed which includes a step in which a primary alcohol, which is a non-reactant, and water, which is a side-reactant are vaporized by the esterification reaction of dicarboxylic acid and a primary alcohol in a reaction device, a step in which the vaporized primary alcohol and water ascends from a lower portion and a liquid-phase primary alcohol descends from an upper portion to be subjected to gas-liquid separation in a column and a gas-phase primary alcohol and water are discharged through an upper portion of the column, a step of recovering heat of the gas-phase primary alcohol and water, and a step of condensing the primary alcohol and water from which the heat has been recovered to be subjected to layer separation.

At this time, the recovered heat is applied to one or more uses of heating the dicarboxylic acid and the primary alcohol before being injected into the reaction device, heating one or more lines selected from the group consisting of a feed line of a purification tower included in the first purification unit, a raw material feed line of the second reaction part, and a feed line of a purification tower included in the second purification unit, and heating condensed water generated in the process.

The production method is performed in the production system including the production unit of a diester-based material described above. Descriptions of the production unit and the heat exchange system thereof applied to the production system and the production method are the same as described above, and thus, the descriptions thereof will be omitted.

EXAMPLES

Hereinafter, the present invention will be described in detail with reference to Examples. However, the following examples are merely illustrative of the present invention and are not intended to limit the scope of the present invention.

In the following Examples and Comparative Examples, a process system according to the method of continuous production of a diester-based material, the method according to the present invention, has been simulated by using CONTINUOUS MODELER in a commercial process simulation program ASPEN PLUS.

Experimental Example 1

In performing simulation using the above program, the simulation has been performed by a production system in which three production units illustrated in FIG. 1 and one production unit illustrated in FIG. 3, and thus, a total of 4 production units are coupled. The order of the production units illustrated in FIG. 3 was applied as shown in Table 1 below, and an applied heat exchanger was also applied as shown in Table 1 below to perform the simulation.

Dicarboxylic acid was terephthalic acid and a primary alcohol was 2-ethylhexanol as raw materials, and the molar ratio of the two raw materials was set to 1:3. The temperature of an organic layer including the primary alcohol discharged through the organic layer line 141 was set to 40° C., and the amount of a coolant consumed in the condenser 15 and the volume of steam used in the entire production system were identified. Values of Table 1 below are relative values (%) assuming that Comparative Example 1 is 100%.

TABLE 1

| | Position of production unit according to present invention | Heat exchange target | Applied diagram | Coolant usage amount | Steam usage amount |
|---|---|---|---|---|---|
| Comparative Example 1 | X | X | FIG. 1 | 100 | 100 |
| Example 1-1 | 1st | Raw material feed line of first reaction part | FIG. 4 | 78 | 50 |

TABLE 1-continued

| | Position of production unit according to present invention | Heat exchange target | Applied diagram | Coolant usage amount | Steam usage amount |
|---|---|---|---|---|---|
| Example 1-2 | 2nd | Raw material feed line of second reaction part | FIG. 5 | 95 | 90 |
| Example 1-3 | 3rd | Purification tower feed line | FIG. 5 | 96 | 92 |
| Example 1-4 | 2nd | Purification tower feed line | FIG. 5 | 88 | 73 |

Referring to Table 1 above, it was confirmed that when a heat exchange system was utilized by applying the production unit according to an embodiment of the present invention to at least one of the four production units, the coolant usage amount and the steam usage amount were greatly reduced.

Experimental Example 2

In performing simulation using the above program, the simulation has been performed by a production system in which three production units illustrated in FIG. 1 and one production unit illustrated in FIG. 3, and thus, a total of 4 production units are coupled. The order of the production units illustrated in FIG. 3 was applied as shown in Table 2 below, and an applied heat exchanger was also applied as shown in Table 2 below to perform the simulation.

Dicarboxylic acid was terephthalic acid and a primary alcohol was 2-ethylhexanol as raw materials, and the molar ratio of the two raw materials was set to 1:3. The temperature of an organic layer including the primary alcohol discharged through the organic layer line 141 was set to 40° C., and the amount of a coolant consumed in the condenser 15 and the amount of energy consumed in producing a utility (high temperature water or steam) in the entire process were identified. Values of Table 2 below are relative values (%) assuming that Comparative Example 1 is 100%.

Referring to Table 2 above, it was confirmed that when a heat exchange system was utilized transmits a applying the production unit according to an embodiment of the present invention to at least one of the four production units, the coolant usage amount and the energy used to produce a utility in the process were greatly reduced.

Experimental Example 3

In performing simulation using the above program, the simulation has been performed by a production system in which two or three production units illustrated in FIG. 1 and one or two production unit illustrated in FIG. 3, and thus, a total of 4 production units are coupled. The order of the production units illustrated in FIG. 3 was applied as shown in Table 3 below, and an applied heat exchanger was also applied as shown in Table 3 below to perform the simulation.

Dicarboxylic acid was terephthalic acid and a primary alcohol was 2-ethylhexanol as raw materials, and the molar ratio of the two raw materials was set to 1:3. The temperature of an organic layer including the primary alcohol discharged through the organic layer line 141 was set to 40° C., and the amount of a coolant consumed in the condenser 15, the volume of steam fed into a reaction vessel, the volume of steam used in the entire production system, and the amount of energy consumed in producing a utility (high temperature water or steam) in the entire process were identified. Values of Table 3 below are relative values (%) assuming that Comparative Example 1 is 100%.

TABLE 2

| | Position of production unit according to present invention | Heat exchange target | Applied diagram | Coolant usage amount | Energy amount required for utility production |
|---|---|---|---|---|---|
| Comparative Example 1 | X | X | FIG. 1 | 100 | 100 |
| Example 1-1 | 2nd | Low pressure steam production | FIG. 6 | 86 | 83 |
| Example 1-2 | 3rd | Low pressure steam production | FIG. 6 | 89 | 87 |
| Example 1-3 | 2nd | High temperature water production | FIG. 6 | 66 | 58 |
| Example 1-4 | 3rd | High temperature water production | FIG. 6 | 78 | 73 |

TABLE 3

| | Position of production unit according to present invention | Heat exchange target | Applied diagram | Coolant usage amount | Steam usage amount | Energy amount required for utility production |
|---|---|---|---|---|---|---|
| Comparative Example 1 | X | X | FIG. 1 | 100 | 100 | 100 |
| Example 3-1 | 3rd | Raw material feed line of first reaction part & Low pressure steam production | FIG. 8 | 89 | 81 | 97 |
| Example 3-2 | 2nd & 3rd | Purification tower feed line & Low pressure steam production | FIG. 9 | 78 | 73 | 87 |
| Example 3-3 | 2nd & 3rd | Purification tower feed line & Low pressure steam production | FIG. 9 | 83 | 92 | 83 |

Referring to Table 3 above, it was confirmed that when a heat exchange system was utilized by applying the production unit according to an embodiment of the present invention to at least one of the four production units, the coolant usage amount, the steam usage amount, and the energy used to produce a utility in the a green process were greatly reduced.

[Description of the Reference Numerals or Symbols]

1, 11, 21: Reaction device
1a, 111, 211: Gas phase discharge line
113, 213: Raw material feed line
2, 12, 22: Column
2a, 121, 221: Gas phase line
4, 14, 24: Layer separator
4a, 141, 241: Organic layer line
5, 15, 25: Condenser
16, 26: Heat exchange device
16b: Second heat exchanger
27: Flash drum
271: Flash drum upper line
LT stream: Low temperature stream
HW/Steam: High temperature water/steam
110, 210: Reaction vessel
112, 212: Product line
120, 220: Column main body
122, 222: Liquid phase line
140, 240: Separation tank
142, 242: Aqueous layer line
16a: First heat exchanger
16c: Third heat exchanger
270: Flash drum main body
272: Flash drum lower line
Condensate: Condensed water

The invention claimed is:

1. A production unit included in a continuous production system of a diester-based material, the production unit comprising:
  a reaction device including a reaction vessel in which an esterification reaction of dicarboxylic acid and a primary alcohol is performed, a raw material feed line for supplying a reactant to the reaction vessel, and a gas phase discharge line installed at an upper end of the reaction vessel such that vaporized primary alcohol and water are discharged to a column therethrough;
  the column including a column main body in which gas-liquid separation of the primary alcohol and the water introduced from the gas phase discharge line is performed, a liquid phase line installed at a lower portion of the column main body such that a liquefied alcohol-rich stream flows into the reaction device, and a gas phase line installed at an upper portion of the column main body and connected to a layer separator such that a mixture stream of a gas-phase primary alcohol and water flows out;
  a heat exchange device installed on the gas phase line of the column and recovering heat of the gas phase line;
  a condenser installed on the gas phase line of the column and installed at a rear end of the heat exchange device and liquefying a mixture of the gas-phase primary alcohol and the water in the gas phase line; and
  the layer separator including a separation tank in which the layer separation of a mixture of the liquefied primary alcohol and the water into an organic layer and an aqueous layer is performed, an organic layer line installed to discharge the separated organic layer to a side upper portion of the column main body, and an aqueous line through which the separated aqueous layer is discharged,
  wherein
  the heat exchange device includes one or more of
  a first heat exchanger installed to transfer heat of the gas phase line of the column to the raw material feed line;
  a second heat exchanger installed to transfer the heat of the gas phase line of the column to a line through which a low temperature stream flows in the continuous production system of a diester-based material; and
  a third heat exchanger installed to transfer the heat of the gas phase line of the column to condensed water generated in the continuous production system of a diester-based material.

2. The production unit of claim 1, wherein:
  the continuous production system of a diester-based material comprises a first reaction part in which a direct esterification reaction is performed, a first purification unit in which a product of the first reaction part is purified, a second reaction part in which a transesterification reaction is performed by introducing the purified product of the first reaction part and an alcohol different from a raw material alcohol of the first reaction part, and a second purification unit in which a product of the second reaction part is purified; and
  the line through which a low temperature stream flows in the continuous production system of a diester-based material comprises a feed line of a purification tower included in each of the first purification unit and the second purification unit and a raw material feed line of the second reaction part.

3. The production unit of claim 1, wherein the heat exchange device comprises the first heat exchanger and the second heat exchanger; the first heat exchanger and the third heat exchanger; or the second heat exchanger and the third heat exchanger sequentially installed on the gas phase line of the column.

4. The production unit of claim 1, further comprising, at a rear-end of the heat exchange device, a flash drum having a flash drum main body in which separation of a liquid phase and a gas phase is performed in the mixture stream including the primary alcohol and the water, a flash drum lower line installed to discharge the liquid phase including a liquefied primary alcohol to the column or the reaction device, and a flash drum upper line installed to discharge the mixture stream of the gas-phase primary alcohol and the water to the layer separator, wherein the gas phase line of the column is connected to a side portion of the flash drum main body, and wherein the condenser is installed on the flash drum upper line.

5. The production unit of claim 1, wherein the temperature of a stream in the gas phase line of the column is 130° C. to 180° C.

6. The production unit of claim 1, wherein the dicarboxylic acid comprises one or more selected from the group consisting of terephthalic acid, phthalic acid, isophthalic acid, and cyclohexane dicarboxylic acid.

7. The production unit of claim 1, wherein the primary alcohol has 3 to 10 carbon atoms.

8. The production unit of claim 1, wherein the esterification reaction is performed at a temperature of 150° C. to 230° C.

9. A method for continuously producing a diester-based material, the method is performed by a continuous production system of a diester-based material, comprising a first reaction part in which a direct esterification reaction is performed, a first purification unit in which a product of the first reaction part is purified, a second reaction part in which a trans-esterification reaction is performed by introducing the purified product of the first reaction part and an alcohol different from a raw material alcohol of the first reaction part, and a second purification unit in which a product of the second reaction part is purified, wherein the first reaction part includes two or more production units connected in series, and in the production unit, a process is performed which includes:

a step in which a primary alcohol, which is a non-reactant, and water, which is a side-reactant, are vaporized by the esterification reaction of dicarboxylic acid and a primary alcohol in a reaction device;

a step in which the vaporized primary alcohol and water ascends from a lower portion and a liquid-phase primary alcohol descends from an upper portion to be subjected to gas-liquid separation in a column and a gas-phase primary alcohol and water are discharged through an upper portion of the column;

a step of recovering heat of the gas-phase primary alcohol and water; and a step of condensing the primary alcohol and water from which the heat has been recovered to be subjected to layer separation, and wherein the recovered heat is applied to one or more uses of:

heating the dicarboxylic acid and the primary alcohol before being injected into the reaction device;

heating one or more lines selected from the group consisting of a feed line of a purification tower included in the first purification unit, a raw material feed line of the second reaction part, and a feed line of a purification tower included in the second purification unit; and heating condensed water generated in the process.

10. A continuous production system of a diester-based material, the system comprising a first reaction part in which a direct esterification reaction is performed, a first purification unit in which a product of the first reaction part is purified, a second reaction part in which a trans-esterification reaction is performed by introducing the purified product of the first reaction part and an alcohol different from a raw material alcohol of the first reaction part, and a second purification unit in which a product of the second reaction part is purified, wherein:

the first reaction part includes two or more of the production unit of claim 1 connected in series; and wherein the heat exchange device includes one or more of:

a first heat exchanger installed to transfer heat to a raw material feed line;

a second heat exchanger installed to transfer the heat to one or more lines selected from the group consisting of a feed line of a purification tower included in the first purification unit, a raw material feed line of the second reaction part, and a feed line of a purification tower included in the second purification unit; and a third heat exchanger installed to transfer the heat to condensed water generated in the process.

11. The continuous production system of claim 10, wherein 3 to 6 of the production units are connected in series.

* * * * *